US010946218B2

(12) United States Patent
Vahala

(10) Patent No.: US 10,946,218 B2
(45) Date of Patent: Mar. 16, 2021

(54) MAGNETIC RESONANCE GUIDED THERAPY WITH INTERLEAVED SCANNING

(71) Applicant: KONINKLIJKE PHILIPS N.V., Eindhoven (NL)

(72) Inventor: Erkki Tapani Vahala, Hyvinkaa (FI)

(73) Assignee: KONINKLUKE PHILIPS N.V., Eindhoven (NL)

( * ) Notice: Subject to any disclaimer, the term of this patent is extended or adjusted under 35 U.S.C. 154(b) by 1030 days.

(21) Appl. No.: 14/400,829

(22) PCT Filed: May 8, 2013

(86) PCT No.: PCT/IB2013/053718
§ 371 (c)(1),
(2) Date: Nov. 13, 2014

(87) PCT Pub. No.: WO2013/171631
PCT Pub. Date: Nov. 21, 2013

(65) Prior Publication Data
US 2015/0126799 A1 May 7, 2015

Related U.S. Application Data

(60) Provisional application No. 61/646,396, filed on May 14, 2012.

(30) Foreign Application Priority Data

May 14, 2012 (EP) .................................... 12167802

(51) Int. Cl.
*A61N 5/10* (2006.01)
*A61B 90/00* (2016.01)

(52) U.S. Cl.
CPC ............. *A61N 5/1037* (2013.01); *A61N 5/10* (2013.01); *A61N 5/107* (2013.01); *A61N 5/1039* (2013.01);
(Continued)

(58) Field of Classification Search
CPC ............ A61B 2090/374; A61N 5/1037; A61N 5/107; A61N 5/1045; A61N 5/1039;
(Continued)

(56) References Cited

U.S. PATENT DOCUMENTS 6,374,132 B1 4/2002 Acker
9,330,490 B2 * 5/2016 Weersink ................ G06T 15/20
(Continued)

FOREIGN PATENT DOCUMENTS

CN 101623198 A 1/2010
WO 2005081842 A2 9/2005
(Continued)

OTHER PUBLICATIONS

Cervino, Laura I. et al "MRI-Guided TUmor Tracking in Lung Cancer Radiotherapy" Physics in Medicine and Biology, vol. 56, 2011, pp. 3773-3785.
(Continued)

*Primary Examiner* — Hien N Nguyen
(74) *Attorney, Agent, or Firm* — Sherry Austin

(57) ABSTRACT

A method for controlling a medical apparatus (100) includes receiving a treatment plan (168) specifying a target volume (146) within an imaging volume (138) and a dose rate of radiation emitted by a radiotherapy apparatus (102). The medical apparatus (100) repeatedly acquires the motion tracking magnetic resonance data and the image magnetic resonance data using an interleaved pulse sequence. The radiotherapy apparatus (102) is controlled to radiate the target volume (146) in accordance with the treatment plan (168). A dose distribution map descriptive of a radiation dose received by the subject (144) from the radiotherapy apparatus (102) is calculated using the motion tracking magnetic resonance data, and the treatment plan (168). A diagnostic image is reconstructed using the image magnetic
(Continued)

resonance data. A display displays the diagnostic image and the dose distribution map. Treatment plan update data is received from a user interface and the treatment plan (168) is updated in accordance with the treatment plan update data.

17 Claims, 3 Drawing Sheets

(52) U.S. Cl.
CPC ......... *A61N 5/1045* (2013.01); *A61N 5/1049* (2013.01); *A61N 5/1077* (2013.01); *A61B 2090/374* (2016.02); *A61N 2005/1055* (2013.01); *A61N 2005/1072* (2013.01); *A61N 2005/1074* (2013.01)

(58) Field of Classification Search
CPC ...... A61N 5/1077; A61N 5/10; A61N 5/1049; A61N 2005/1074; A61N 2005/1072; A61N 2005/1055
See application file for complete search history.

(56) References Cited

U.S. PATENT DOCUMENTS

| | | | |
|---|---|---|---|
| 2003/0050557 A1 | 3/2003 | Susil | |
| 2006/0293598 A1 | 12/2006 | Fraser | |
| 2007/0244386 A1 | 10/2007 | Steckner | |
| 2008/0081991 A1* | 4/2008 | West | A61N 5/1031 600/425 |
| 2009/0052623 A1* | 2/2009 | Tome | G06Q 50/22 378/65 |
| 2009/0175418 A1* | 7/2009 | Sakurai | A61N 5/1048 378/98.5 |
| 2010/0106005 A1 | 4/2010 | Karezmar | |
| 2010/0317961 A1 | 12/2010 | Jenkins | |
| 2011/0130644 A1* | 6/2011 | Stemmer | A61B 5/055 600/410 |
| 2011/0144495 A1* | 6/2011 | Wilkening | A61B 8/0883 600/443 |
| 2011/0234222 A1* | 9/2011 | Frahm | G01R 33/4824 324/309 |
| 2012/0165652 A1* | 6/2012 | Dempsey | A61N 5/1045 600/411 |
| 2013/0021030 A1* | 1/2013 | Zuehlsdorff | G01R 33/48 324/309 |
| 2013/0077752 A1* | 3/2013 | Zankowski | A61N 5/1031 378/65 |
| 2013/0102830 A1 | 4/2013 | Otto | |
| 2013/0245425 A1 | 9/2013 | Dempsey | |

FOREIGN PATENT DOCUMENTS

| | | |
|---|---|---|
| WO | 2011127947 A1 | 10/2011 |
| WO | 2013030746 A1 | 3/2013 |

OTHER PUBLICATIONS

Khoo, V.S. et al "New Developments in MRI for Target Volume Delineation in Radiotherapy", The British Journal of Radiology, vol. 79, 2006, pp. S2-S15.

Hissoiny et al., "Fast Dose Calculation in Magnetic Fields with GPUMCD", Physics in Medicine and Biology, 56 (2011) 5119-5129.

Knöös, "Dose Planning and Dose Delivery in Radiation Therapy", Lund University, Malmö1991 SE, 44 pg.

* cited by examiner

MAGNETIC RESONANCE GUIDED THERAPY WITH INTERLEAVED SCANNING

CROSS-REFERENCE TO PRIOR APPLICATIONS

This application is the U.S. National Phase application under 35 U.S.C. § 371 of International Application No. PCT/IB2013/053718, filed on May 8, 2013, which claims the benefit of U.S. Provisional Patent Application No. 61/646,396, filed on May 14, 2012 and European Patent Application No. 12167802.3, filed on May 14, 2012. These applications are hereby incorporated by reference herein.

TECHNICAL FIELD

The invention relates to apparatuses for treating a target zone of a subject with radiotherapy, in particular the invention relates to radiotherapy apparatuses guided by magnetic resonance imaging.

BACKGROUND OF THE INVENTION

Integrated magnetic resonance imaging (MRI) and Linear Accelerators (LINAC) system image guidance during radiotherapy has become increasingly important and has gained wide application during the last years. The aim of the system is to deliver a precise radiation dose to a selected target within the interior of the body based on diagnostic quality MR images. Typically, a LINAC source is placed on a rotating gantry about the magnet of an MRI apparatus and the magnet is designed such that the LINAC rotates in a zero-field region of the magnet.

The exact knowledge about the position of the treat region permits an accurate spatial (and temporal) beam spot of that system in the range of millimeters to effectively irradiate the target.

U.S. Pat. No. 6,374,132 B1 discloses a method to monitor hyperthermia treatments such as tissue ablation by using magnetic resonance information acquired by a movable magnetic resonance instrument.

SUMMARY OF THE INVENTION

Embodiments of the invention may provide for a method for updating a treatment plan of a medical apparatus based on motion tracking magnetic resonance data and image magnetic resonance data, a medical apparatus and a computer program product.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic resonance image data (such as motion tracking magnetic resonance data or image magnetic resonance data used herein) is defined as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

In one aspect, the invention relates to a medical apparatus comprising a radiotherapy apparatus for radiating a target volume; a magnetic resonance module for acquiring motion tracking magnetic resonance data and image magnetic resonance data from a subject of which at least a part is located within an imaging volume, wherein the target volume is within the imaging volume; a memory for storing machine executable instructions; and a processor for controlling the medical apparatus, wherein execution of the machine executable instructions causes the processor to receive a treatment plan specifying the target volume within the imaging volume and a dose rate of radiation emitted by the radiotherapy apparatus, and to repeatedly:

acquire the motion tracking magnetic resonance data and the image magnetic resonance data by controlling the magnetic resonance module with an interleaved pulse sequence;

control the radiotherapy apparatus to radiate the target volume in accordance with the treatment plan;

calculate a dose distribution map descriptive of a radiation dose received by the subject from the radiotherapy apparatus using the motion tracking magnetic resonance data, and the treatment plan;

reconstruct a diagnostic image using the image magnetic resonance data;

display on a display the diagnostic image and the dose distribution map;

receive treatment plan update data from a user interface; and update the treatment plan in accordance with the treatment plan update data.

Said features may be advantageous in that they provide the required information for an accurate radiation therapy planning. In fact, the magnetic resonance module provides the diagnostic images of clinically high quality for visualizing the target volume. These images are produced with high spatial resolution, high signal-to-noise and/or enhanced contrast. However, the target volume may experience motion such as gross patient movement, peristaltic or respiratory motion. In order to track the movement of the target volume, movement-related data (i.e. motion tracking magnetic resonance data) are also acquired with the image magnetic resonance data in an interleaved pulse sequence. The motion tracking magnetic resonance data are produced with high temporal resolution compared to the image magnetic resonance data. It is noted that the magnetic resonance signals are acquired from the part of the subject that is located in the imaging volume. In the imaging volume, spins in the part of the subject are excited and generate magnetic resonance signals. In general the subject, e.g. a patient to be examined, as a whole is larger than the imaging volume. However, generally there is no need to acquire magnetic resonance signals from the entire body of the patient, and it is sufficient that the part of the subject that is to be examined, e.g. a part of the anatomy that is of interest is located in the imaging volume and from which the magnetic resonance signals are acquired.

Another advantage being that said information may be used to update the treatment plan on the fly. The diagnostic images are displayed together with the dose distribution map to a user of the medical device. An exemplary technique for calculating a dose distribution map is set forth in "Fast Dose Calculation in Magnetic Fields with GPUMCD", Hissoiny et al., Physics in Medicine and Biology, 56 (2011) 5119-5129. The user may decide to abort or correct the treatment plan on the fly if the dose accumulation does not match the expectations. This may be due for example to an accumulated dose which exceeds a pre-defined dose range accepted on the target volume. The user may perform a request by entering a command via an input device of the medical device. The treatment plan is therefore updated to match the actual position of the target volume. This position is precisely provided by tracking the motion of the target using the motion tracking data. The exact knowledge about the target position permits an accurate spatial (and temporal) beam spot of the radiotherapy apparatus in the range of millimeters to effectively irradiate the target volume without affecting the surrounding tissues and critical structures. This may increases patient safety and reduces the treatment time.

A further advantage being that the repeated acquisition of data provides image data that are up to date with the ongoing target motion and deformation.

According to one embodiment, the execution of the instructions further causes the processor to reconstruct low temporal resolution images using the image magnetic resonance data, and to reconstruct high temporal resolution images using the motion tracking magnetic resonance data.

The motion tracking magnetic resonance data are acquired on short time periods so as the different motion states of the target may reliably be tracked. The image magnetic resonance data are acquired on a longer time period such that the resulting diagnostic image is of high quality for visualization. For example, the motion tracking image may be produced in a coronal view to continuously monitor the position of the target volume during respiration.

According to one embodiment, the motion tracking magnetic resonance data are acquired using one-dimensional navigator pencil-beam.

According to one embodiment, the image magnetic resonance data are acquired from beams eye view planes by controlling the magnetic resonance module. This allows an easy comparison with the treatment plan that has also been created using said views.

According to one embodiment, the treatment plan update data comprises a request to automatically update the treatment plan using the dose distribution map, wherein the treatment plan is updated at least partially in accordance with the dose distribution map.

In case the displayed accumulated dose doesn't match the expectation, the initial dose rate specified in the treatment plan has to be re-calculated based on the dose distribution map.

According to an alternative embodiment, the update of the treatment plan may be performed using a pre-calculated atlas method that uses a prior knowledge of the subject anatomy in relation to the target volume. That is, separate treatment plans are created for permutations of expected target positions. These treatment plans may have different radiation doses and/or various treatment device settings such as radiation intensity, wherein each of the treatment plans is associated with a pre-defined target image. The current motion tracking image obtained from the motion tracking data may be matched to these pre-defined target images in order to find the closest acceptable atlas match which indicates a treatment plan to replace the initial treatment plan. The matching comprises comparing a location of the center of the target volume in the motion tracking image and each of the pre-defined target images.

The so-called inverse planning simulated annealing algorithm may also be used to automatically find an optimal treatment plan based on the current position of the target volume and user's prescription for dose distribution. The dose distribution may comprise dose calculation points generated on the contour of the target volume and the dose calculation points generated inside the target volume.

According to one embodiment, the treatment plan update data is used at least partially to directly update the treatment plan. This is advantageous as it further saves the treatment time and CPU time to update the treatment plan that would otherwise be required by the medical apparatus application.

According to one embodiment, the medical apparatus further comprises a multi-leaf collimator for collimating a radiation beam of the therapeutic apparatus to an irradiation area in match with the target volume, wherein the treatment plan update data comprises a request to automatically update the treatment plan by adjusting the multi-leaf collimator to match the target volume using the motion tracking magnetic resonance data. The treatment plan may be updated by specifying the coordination between radiation delivery and leaf adjustments so as to meet the current target position. The adjustment comprises the orientations of beams and the number of apertures per beam angle. This update of the treatment plan may be performed using the pre-calculated atlas method and/or inverse planning simulated annealing algorithm.

According to one embodiment, the radiotherapy apparatus is controlled to radiate the target volume in accordance with the treatment plan and the motion tracking magnetic resonance data. This is advantageous, because the radiation delivered to the target is up to date with the ongoing target motion.

According to one embodiment, the dose distribution map and the diagnostic image are displayed side by side.

According to one embodiment, the dose distribution map and the diagnostic image are overlaid.

According to one embodiment, the execution of the instructions further causes the processor to acquire the image magnetic resonance data during a pre-determined part of a cyclic motion of the subject by controlling the magnetic resonance module. An example of the cyclic motion is a respiratory cycle. The pre-determined part may be a quiet phase of the cycle.

After extracting timing information from respiratory signals, the acquisition is triggered at the same phase of each cycle and only during cycles that occur during the pre-determined part. The exact phase can be varied to reduce cumulative magnetization effects.

These embodiments may be advantageous as they improve the contrast and spatial resolution of the diagnostic images and reduce the blurring of the said images.

According to one embodiment, the update of the treatment plan occurs during radiation of the target volume. The total dose radiation is usually broken into a number of radiation therapy fractions during which the treatment is delivered and the target is irradiated. During the radiation therapy fraction, the processor may receive a request to update the treatment plan and thus update the treatment plan during said radiation therapy fraction. This embodiment is advantageous, because it updates the treatment plan very early based on the current target position information. This may lead to better and more efficient treatments than if the treatment plan were adjusted after the radiation therapy fraction is finished.

According to one embodiment, the radiotherapy apparatus is controlled to radiate the target volume in separate radiation therapy fractions, wherein the update of the treatment plan occurs after one of the radiation therapy fractions is finished.

According to one embodiment, the radiotherapy apparatus comprises a LINAC X-ray source for radiating the target volume.

According to one embodiment, the radiotherapy apparatus further comprises an X-ray tube, a radio isotope gamma radiation source, a carbon nanotube X-ray source, a proton beam source, charged particle beam source, a neutron beam source, and a carbon ion source.

According to one embodiment, the execution of the instructions further causes the processor to calculate the dose distribution map using the motion tracking magnetic resonance data, radiotherapy apparatus output data and the treatment plan. The radiotherapy apparatus output data comprises beam shape and/or radiation intensity.

In another aspect, the invention relates to a computer program product containing machine executable instructions for execution by a processor controlling a medical apparatus, wherein the medical apparatus comprises a radiotherapy apparatus for radiating a target volume; a magnetic resonance module for acquiring motion tracking magnetic resonance data and image magnetic resonance data from a subject located within an imaging volume, wherein the target volume is within the imaging volume; wherein execution of the machine executable instructions causes the processor to receive a treatment plan specifying the target volume within the imaging volume and a dose rate of radiation emitted by the radiotherapy apparatus, and to repeatedly:

acquire the motion tracking magnetic resonance data and the image magnetic resonance data by controlling the magnetic resonance module with an interleaved pulse sequence;

control the radiotherapy apparatus to radiate the target volume in accordance with the treatment plan;

calculate a dose distribution map descriptive of a radiation dose received by the subject from the radiotherapy apparatus using the motion tracking magnetic resonance data, and the treatment plan;

reconstruct a diagnostic image using the image magnetic resonance data;

display on a display the diagnostic image and the dose distribution map;

receive treatment plan update data from a user interface; and update the treatment plan in accordance with the treatment plan update data.

In another aspect, the invention relates to a method of controlling a medical apparatus, wherein the medical apparatus comprises a radiotherapy apparatus for radiating a target volume; a magnetic resonance module for acquiring motion tracking magnetic resonance data and image magnetic resonance data from a subject located within an imaging volume, wherein the target volume is within the imaging volume, wherein the method comprises receiving a treatment plan specifying the target volume within the imaging volume and a dose rate of radiation emitted by the radiotherapy apparatus, and repeatedly:

acquiring the motion tracking magnetic resonance data and the image magnetic resonance data by controlling the magnetic resonance module with an interleaved pulse sequence;

controlling the radiotherapy apparatus to radiate the target volume in accordance with the treatment plan;

calculating a dose distribution map descriptive of a radiation dose received by the subject from the radiotherapy apparatus using the motion tracking magnetic resonance data, and the treatment plan;

reconstructing a diagnostic image using the image magnetic resonance data;

displaying on a display the diagnostic image and the dose distribution map;

receiving treatment plan update data from a user interface; and updating the treatment plan in accordance with the treatment plan update data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Figure 1:
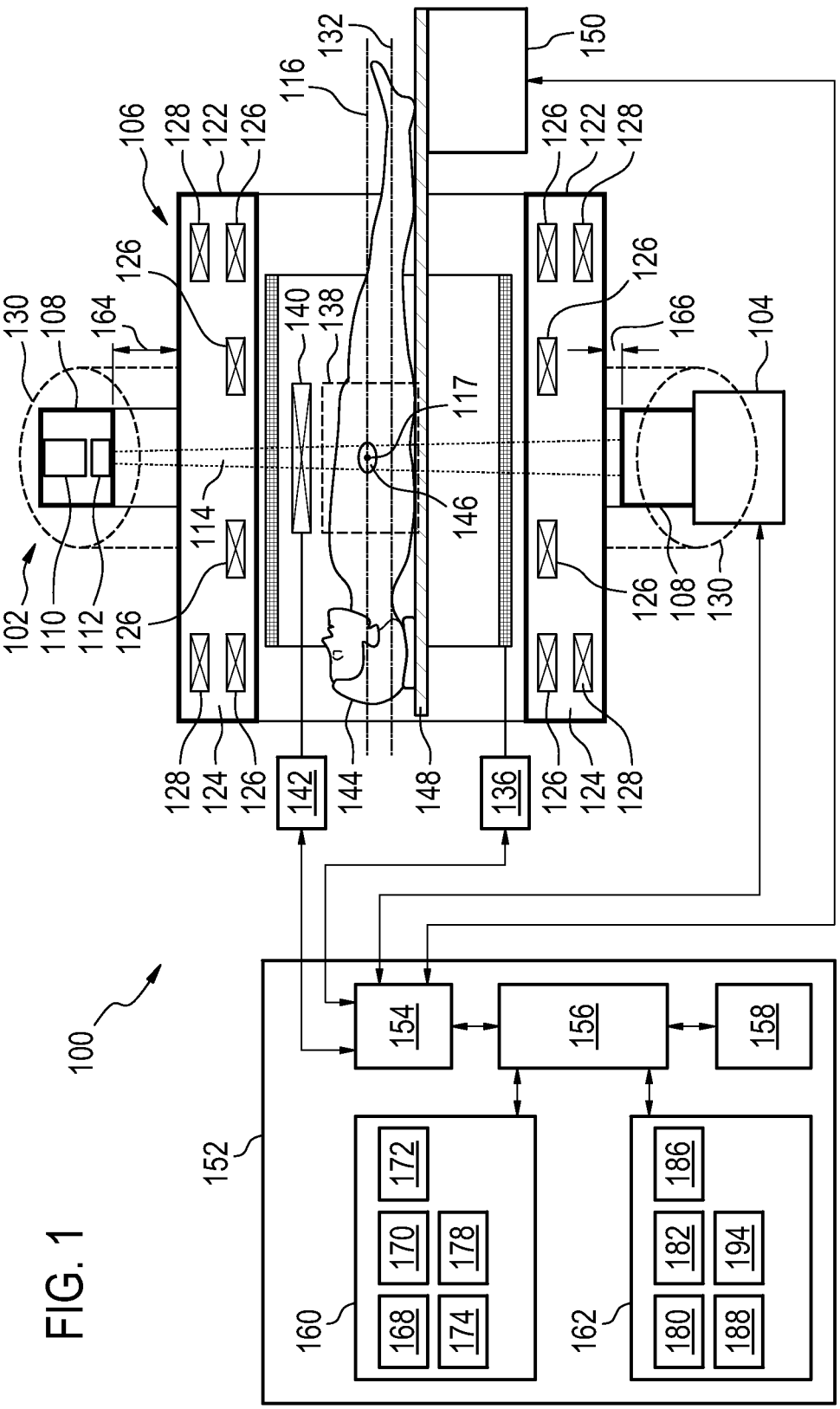
FIG. 1 shows a cross-sectional and functional view of a medical apparatus.

FIG. 1 shows a cross-sectional and functional view of a medical apparatus 100. The medical apparatus 100 is shown as comprising a radiotherapy apparatus 102 and a magnetic resonance imaging module 106. The radiotherapy apparatus 102 comprises a ring mechanism 108. The ring mechanism 108 supports a radiotherapy source 110. The radiotherapy source 110 is representative and may be a LINAC x-ray source, an x-ray 2 and a radioisotope gamma radiation source. Adjacent to the radiotherapy source 110 is a multi-leaf beam collimator 112 for collimating a radiation beam 114 that is generated by the radiotherapy source 110. The ring mechanism 108 is also adapted for rotating the radiotherapy source 110 and the beam collimator 112 about a rotational point 117 of the radiotherapy apparatus 102. A rotational axis 116 passes through the rotational point 117.

The magnetic resonance imaging module 106 is shown as comprising a magnet 122. The ring mechanism 108 is ring-shaped and surrounds the magnet 122. The magnet 122 shown in FIG. 1 is a cylindrical type superconducting magnet. However, other magnets are also applicable for embodiments of the invention. The magnet 122 has a supercooled cryostat 124. Inside the cryostat 124 there is a collection of superconducting coils 126. There are also compensation coils 128 whose current opposes the direction of current in the superconducting coils 126. This creates a low magnetic field zone 130 that circles or encompasses the magnet 122. The cylindrical magnet 122 is shown as having an axis 132 of symmetry.

Within the bore of the magnet there is a magnetic field gradient coil 134 which is used for acquisition of motion tracking magnetic resonance data and image magnetic resonance data to spatially encode objects within an imaging volume 138 of the magnet 122. The magnetic field gradient coil 134 is connected to a magnetic field gradient coil power supply 136. The magnetic field gradient coil 134 is intended to be representative. Typically magnetic field gradient coils contain three separate sets of coils for spatially encoding in three orthogonal spatial directions. The imaging volume 138 is located in the center of the magnet 122.

Adjacent to the imaging volume 138 is a radio frequency coil 140 for manipulating the orientations of magnetic spins within the imaging volume 138 and for receiving radio transmissions from spins also within the imaging volume 138. The radio frequency coil 140 is connected to a radio frequency transceiver 142. The radio frequency coil 140 and radio frequency transceiver 142 may be replaced by separate transmit and receive coils and a separate transmitter and receiver. It is understood that the radio frequency coil 140 and the radio frequency transceiver 142 are simply representative.

Within the center of the magnet is also located a subject 144. The subject 144 has a target volume 146 and is shown as reposing on a subject support 148. The subject support 148 has a mechanical positioning system 150. The mechanical positioning system is adapted for positioning the subject 144 within the magnet 122. Depending upon the space available inside of the magnet the subject support 148 may be adapted for moving the subject in different directions. A mechanical positioning system 150 may move the subject support in a direction perpendicular to the magnet axis 132. If there is more space available inside the magnet the mechanical positioning system 150 may have more degrees of freedom. For instance the mechanical positioning system 150 may position the subject support 148 with six degrees of freedom. The radio frequency transceiver 142, the magnetic field gradient coil power supply 136, the mechanical actuator 104, and the mechanical positioning system 150 are all shown as being connected to a hardware interface 154 of a computer system 152. The computer system 152 uses a processor 156 to control the medical apparatus 100.

The computer system 152 shown in FIG. 1 is representative. Multiple processors and computer systems may be used to represent the functionality illustrated by this single computer system 152. The computer system 152 comprises the hardware interface 154 which allows the processor 156 to send and receive messages to components of the medical apparatus 100. The processor 156 is also connected to a user interface 158, computer storage 160, and computer memory 162. The radiotherapy apparatus 102 is not shown as being connected to the hardware interface 154. The radiotherapy apparatus 102 may be, for example, connected to the hardware interface 154 and communicates with the computer system 152 via the mechanical actuator 104.

For the example shown in FIG. 1, the rotational axis 116 of the radiotherapy apparatus is not coaxial with the magnet axis 132. The rotational point 117 is shown as being off center from the magnet axis 132. It can be seen that the target zone 146 is off-center and away from the magnet axis 132. The radiotherapy apparatus 102 has been moved by mechanical actuator 104 such that the rotational point 117 of the radiotherapy apparatus is within the target zone 146. It can be seen that the ring mechanism 108 has been moved relative to the magnet 122. The arrow 164 indicates a top distance between the inside of the ring mechanism 108 and arrow 166 indicates a distance between the magnet 122 and the bottom inside of the ring mechanism 108. The distance 166 is shorter than the distance 164 and it can be seen that the rotational point 117 is above the magnet axis 132. The radiation beam 114 passes through the rotational point 117. Placing the rotational point 117 at the center of the target zone 146 allows the target zone to be treated continuously when the radiation beam 114 is created by the radiotherapy source 110 and is rotated by the ring mechanism 108.

Computer storage 160 is shown as containing a treatment plan 168. The treatment plan 168 contains instructions or a plan for treating the target volume 146. The treatment plan 168 may contain details of the subject anatomy 144 in relation to the target volume 146. The computer storage 160 is further shown as containing image magnetic resonance data and motion tracking magnetic resonance data 170 that have been acquired by the magnetic resonance imaging module 106. The computer storage 160 is shown as further containing diagnostic images and motion tracking images 172 that have been reconstructed from the image magnetic resonance data and tracking motion magnetic resonance data respectively. The computer storage 160 is shown as further containing coordinates 174 of the target volume 146. The computer storage 160 is shown as further containing radiotherapy control signals 178.

The computer memory 162 contains machine executable instructions 180, 182, 186, 188, 194 for operation by the processor 156. The computer memory 162 is shown as containing a medical apparatus control module 180. The medical apparatus control module 180 contains machine executable instructions which allow the processor 156 to control the overall functioning of the medical device 100. The computer memory 162 is shown as further containing a radiotherapy apparatus control module 182. The radiotherapy apparatus control module 182 contains machine executable instructions which allow the processor 156 to control the functioning of the radiotherapy apparatus 102.

The computer memory 162 is shown as further containing a magnetic resonance imaging control module 186. The magnetic resonance imaging control module contains machine executable code which allows the processor 156 to control the functioning and operation of the magnetic resonance imaging module 106. The computer memory 162 is shown as further containing an image reconstruction module 188. The image reconstruction module 188 contains machine executable code which is used by the processor 156 to transform the motion tracking and image magnetic resonance data 170 into respective images 172.

The computer memory 162 is shown as further containing radiotherapy control signal generation module 194. The radiotherapy control signal generation module 194 contains computer executable code which the processor 156 uses to generate the radiotherapy control signals 178. The radiotherapy control signals 178 may be generated in conjunction with the coordinates of the target volume 174, and the treatment plan 168.

Figure 2:
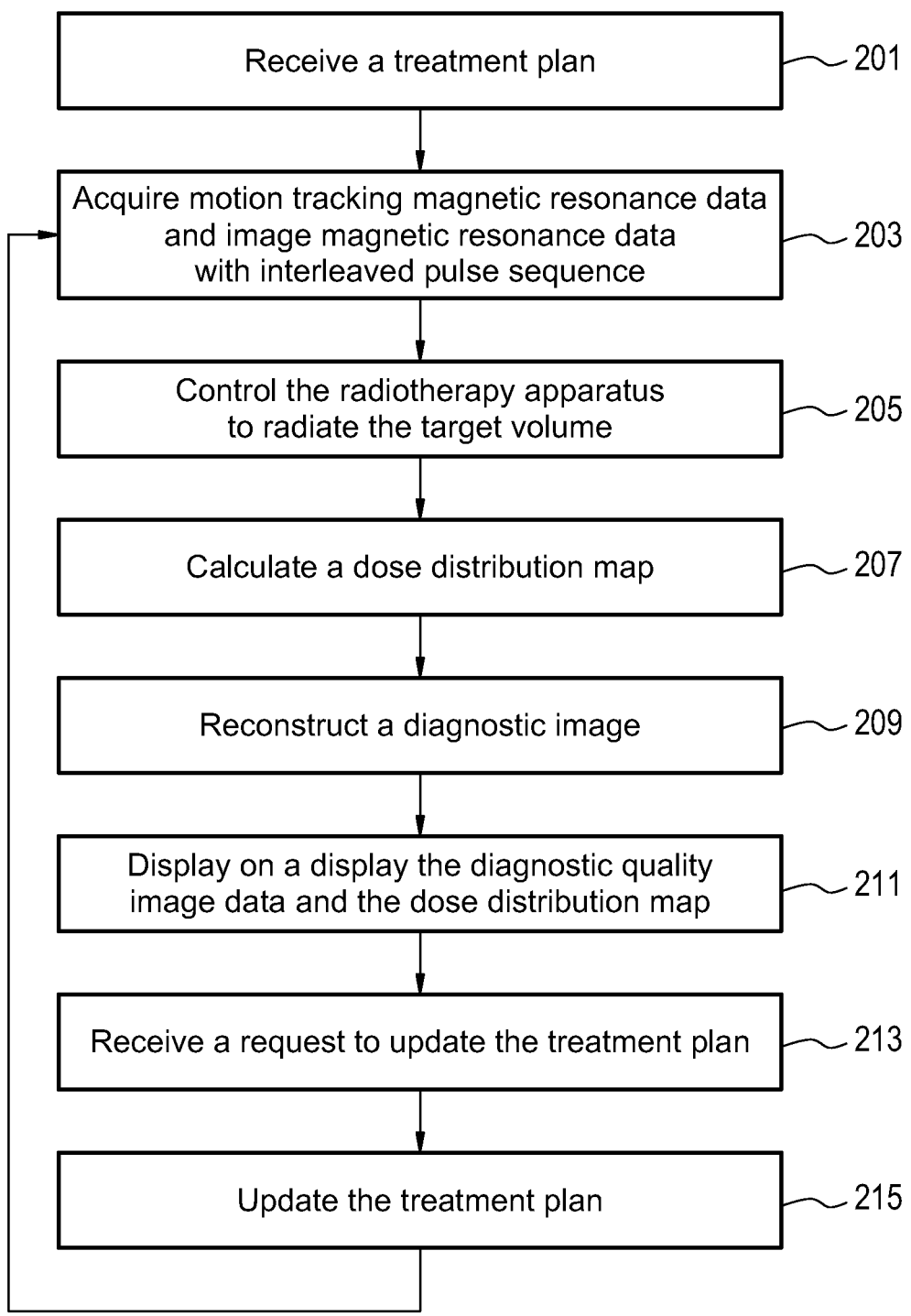
FIG. 2 is a flowchart of a method of controlling a medical apparatus.

FIG. 2 is a flowchart of a method for controlling a medical device 100. In step 201 the processor 156 of the computer system 162 receives a treatment plan specifying a target volume 174 within the imaging volume 138 and a dose rate of radiation emitted by the radiotherapy apparatus 102. MRI module 106 may provide information on the localization of the target volume 174 and the surrounding tissues. Before the intervention, a treatment planning algorithm such as the pre-calculated atlas may be used to determine the initial treatment plan. Using said information, a plan of the optimal distribution of the radiation sources can be developed which may include consideration of how the multi-leaf collimator should be placed and positioned.

In step 203, the processor 156 acquires motion tracking magnetic resonance data and image magnetic resonance data from nuclei of the subject 144 located within the imaging volume 138 by controlling the magnetic resonance module 106. The imaging may be performed in one or more interleaved 2D imaging samples, and a coronal view may be used to continuously monitor the position of the target volume during respiration for example. The motion tracking magnetic resonance data are acquired on short time periods so as the different motion states of the target may reliably be tracked. The image magnetic resonance data are acquired on a longer time period such that the resulting image is of high quality for visualization. The image magnetic resonance data may be acquired during a pre-determined part of a respiratory cycle of the subject by controlling the magnetic resonance module. The pre-determined part may be a quiet phase of the respiratory cycle. The acquisition may be triggered after extracting timing information from respiratory signals. The acquisition may also be triggered at the same phase of each cardiac cycle and only during cardiac cycles that occur during the pre-determined part. The exact phase may be varied to reduce cumulative magnetization effects.

In step 205, the processor 156 controls the radiotherapy apparatus to radiate the target volume in accordance with the treatment plan. The radiotherapy apparatus may also radiate the target volume in accordance with the target volume and the motion tracking magnetic resonance data.

In step 207, the processor 156 calculates a dose distribution map descriptive of a radiation dose received by the subject from the radiotherapy apparatus using the motion tracking magnetic resonance data, radiotherapy apparatus output data, and the treatment plan. A suitable technique for calculating the dose distribution map is set forth in "Fast Dose Calculation in Magnetic Fields with GPUMCD", Hissoiny et al., Physics in Medicine and Biology, 56 (2011) 5119-5129. That is, the dose is a function of current position of the target and the current radiotherapy apparatus output data. The radiotherapy apparatus output data comprises beam shape and/or radiation intensity. The current position of the target volume as it moves through a sequence of the motion tracking images may be estimated by detecting the motion of the target volume from the sequence of the motion tracking images. For example, this may be performed by first defining an initial target volume position in the first acquisitioned image of the sequence of the motion tracking images. The position may be defined by the pixel locations of the pixels delimiting the target volume. Pixels locations of the target volume 146 are also defined for each image of the following sequence of the motion tracking images. In tracking, a transformation function may be estimated throughout the sequence of images to determine the change in the pixel locations and thus the motion path of the target volume 146. The transformation function may depend, for example, on the image acquisition time. The treatment plan may be updated using methods such as inverse planning by simulated annealing or a pre-calculated atlas method.

In step 209, the processor reconstructs a diagnostic image using the image magnetic resonance data. In step 211, the processor displays the diagnostic image and the dose distribution map to a user of the medical apparatus 100. The display may show the delineated target and organs at risk and the dose distribution in space to be expected with the current target position and/or the planned dose rate. The diagnostic image and the dose distribution map may be displayed side by side or be overlaid in a single image.

Based on an analysis of the displayed image, the user may decide to abort or correct the treatment plan on the fly if the dose accumulation does not match the expectations. That is, the processor 156 receives, in step 213, a treatment plan update data from a user interface. For example, the user may enter via the user interface the data necessary to directly and at least partially update the treatment plan. In another example, the user may enter a request (or command) via the user interface to automatically and at least partially update the treatment plan using the dose distribution map or by adjusting the multi-leaf collimator 112. This can be realized by an input device such as a mouse, a touchpad, a button or the like.

In step 215, the processor 156 updates the treatment plan in accordance with the treatment plan update data. In this flowchart there is an arrow that looks back from step 215 to step 203. This indicates that during the treatment data may be repeatedly acquired and used to repeatedly update the treatment plan using the repeatedly updated data.

Figure 3:
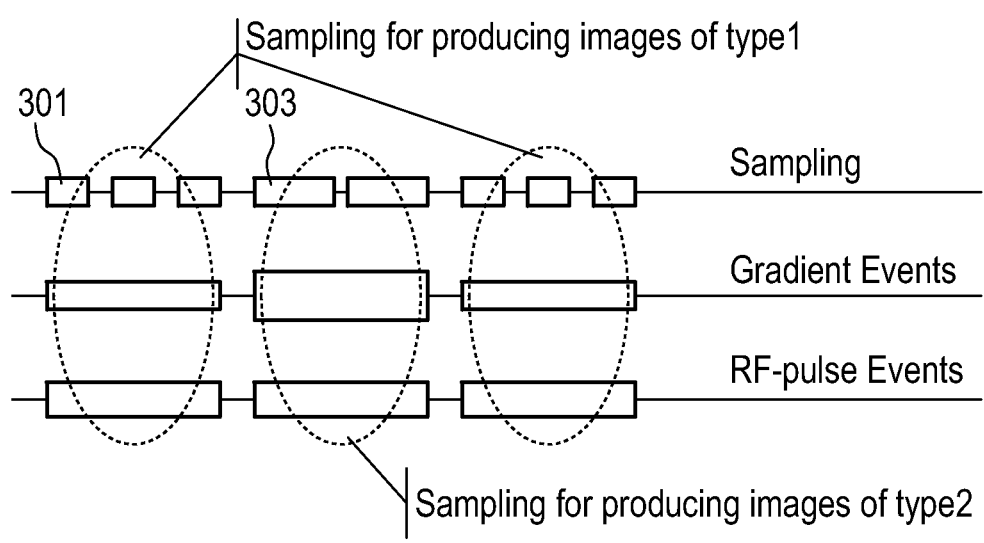
FIG. 3 illustrates a simplified schematic view of a sampling diagram of an interleaved image acquisition.

FIG. 3 illustrates a simplified schematic view of a sampling diagram of an interleaved image acquisition to describe the step 203 of FIG. 2. K-space is sampled for producing images with different temporal and morphological characteristics. Two different image types are being acquired in interleaved pulse sequence during an acquisition time. The drawing can be further generalized by adding multiple different sampling sections for more image types. The number of sampling sections is limited by available acquisition time. Image type 1 acquires 3 time samples 301 with its typical gradient and RF pulse configuration, followed by two time samples 303 for the image type 2, after which the type 1 is continued etc. These samples of each image type may be accumulated to reconstruct an image. Images type 1 and type 2 are acquired with different types of contrast, typically at different time intervals. In another example, an image of type 1 may be fully acquired before part of image type 2 is sampled. An image may be constructed with a single sample (e.g., single shot EPI sequence). In a further example, samples are reused so that image types share sampling sections to provide hybrid images. For example, the samples from another image type are used to update the samples near k-space center of another, less often sampled type, in order to provide keyhole-like behavior, where the contrast is typical for the latter type but the images are produced more often and indicate gross patient movement/big changes in morphology.

LIST OF REFERENCE NUMERALS 100 medical apparatus
102 radiotherapy apparatus
104 mechanical actuator
106 magnetic resonance imaging module
108 ring mechanism
110 radio therapy source
112 multi-leaf beam collimator
114 radiation beam
116 rotational axis
117 rotational point
122 magnet
124 cryostat
126 superconducting coil
128 compensation coil
130 low magnetic field zone
132 magnet axis
134 magnetic field gradient coil
136 magnetic field gradient coil power supply
138 imaging volume
140 radio frequency coil
142 radio frequency transceiver
144 subject
146 target volume
148 subject support
150 mechanical positioning system
152 computer system
154 hardware interface
156 processor
158 user interface
160 computer storage
162 computer memory
164 top distance
166 bottom distance
168 treatment plan
170 image magnet resonance data and motion tracking magnetic resonance data
172 diagnostic images and motion tracking images
174 coordinates of target volume
178 radio therapy control signals
180 therapeutic apparatus control module
182 radio therapy apparatus control module
186 magnetic resonance imaging control module
188 image reconstruction module
194 radio therapy control signal generation module
201-215 steps
301-303 time samples of type 1 and type 2.

The invention claimed is:

1. A medical apparatus comprising:
a radiotherapy apparatus configured to radiate during a treatment fraction a target volume undergoing motion during a treatment fraction;
a magnetic resonance scanner configured to acquire motion tracking magnetic resonance data and image magnetic resonance data from a subject of which at least a part is located within an imaging volume undergoing subject motion, wherein the target volume is within the imaging volume, the motion tracking magnetic resonance data having a higher temporal resolution than the image magnetic resonance data and being indicative of a path of target volume positions during the subject motion;
a memory configured to store machine executable instructions; and
a processor configured to execute the machine executable instructions, wherein executing the machine readable instructions causes the processor to receive a treatment plan specifying a radiation dose distribution to be delivered to the target volume within the imaging volume and a dose rate of radiation emitted by the radiotherapy apparatus, and to repeatedly during a treatment fraction:
acquire the higher temporal resolution motion tracking magnetic resonance data and the image magnetic resonance data from the imaging volume from a subject undergoing subject motion by controlling the magnetic resonance scanner with an interleaved magnetic resonance pulse sequence that interleaves the higher temporal resolution motion tracking magnetic resonance data and the image magnetic resonance data during the magnetic resonance pulse sequence;
control the radiotherapy apparatus to radiate the target volume in the imaging volume in accordance with the treatment plan;
calculate a dose distribution map descriptive of a radiation dose received by the target volume from the radiotherapy apparatus
reconstruct a higher resolution diagnostic image using the lower temporal resolution image magnetic resonance data;
control a display apparatus to display the higher resolution diagnostic image and the dose distribution map descriptive of a radiation dose received by the target volume and the image volume;

receive treatment plan update data from a user interface; and update the treatment plan in accordance with the treatment plan update data.

2. The medical apparatus of claim 1, wherein the treatment plan update data comprises a request to automatically update the treatment plan using the dose distribution map, wherein the treatment plan is updated at least partially in accordance with the dose distribution map.

3. The medical apparatus of claim 1, wherein the treatment plan is updated during radiation of the target volume according to the treatment plan.

4. The medical apparatus of claim 2, further comprises a multi-leaf collimator for collimating a radiation beam of the therapeutic apparatus to an irradiation area in match with the target volume, wherein the treatment plan update data comprises a request to automatically update the treatment plan by adjusting the multi-leaf collimator to match the target volume using the motion tracking magnetic resonance data.

5. The medical apparatus of claim 1, wherein the processor is configured to control the magnetic resonance scanner to continuously monitor a position of the target volume during a treatment fraction.

6. The medical apparatus of claim 4, wherein the dose distribution map and the diagnostic image are displayed side by side.

7. The medical apparatus of claim 1, wherein the high temporal resolution images of the dose distribution map and the high resolution diagnostic image are displayed overlaid.

8. The medical apparatus of claim 6, wherein the execution of the instructions further causes the processor to acquire the higher temporal resolution image magnetic resonance data during a pre-determined part of a cyclic motion of the subject by controlling the magnetic resonance scanner.

9. The medical apparatus of claim 4, wherein the update of the treatment plan occurs during radiation of the target volume based on a current position of the target volume.

10. The medical apparatus of claim 9, wherein the radiotherapy apparatus comprises a linear accelerator (LINAC) configured to irradiate the target volume.

11. A non-transitory computer-readable medium carrying machine executable instructions for execution by a processor controlling a medical apparatus, wherein the medical apparatus comprises a radiotherapy apparatus for radiating a target volume; a magnetic resonance module for acquiring two types of data namely motion tracking magnetic resonance data and image magnetic resonance data from a subject of which at least a part is located within an imaging volume, wherein the target volume is within the imaging volume; wherein execution of the machine executable instructions causes the processor to receive a treatment plan specifying the target volume, the imaging volume and a dose rate of radiation emitted by the radiotherapy apparatus, and in each of a plurality of fractions to repeatedly:

acquire the motion tracking magnetic resonance data and the image magnetic resonance data by controlling the magnetic resonance module with an interleaved pulse sequence which interleaves motion tracking magnetic resonance data acquisition with image magnetic resonance data acquisition to continuously monitor a motion path of the target volume, the motion tracking magnetic resonance data has a higher temporal resolution than the image magnetic resonance data;

control the radiotherapy apparatus to radiate the target volume in accordance with the treatment plan;

calculate a radiation dose distribution map descriptive of a radiation dose received by the subject from the radiotherapy apparatus;

reconstruct a diagnostic image using the lower temporal resolution image magnetic resonance data;

control a display to display the diagnostic image and the dose distribution map;

receive treatment plan update data from a user interface; and update the treatment plan in accordance with the treatment plan update data.

12. A method of controlling a medical apparatus, wherein the medical apparatus comprises a radiotherapy apparatus configured to irradiate a target volume; a magnetic resonance scanner configured to acquire motion tracking magnetic resonance data and image magnetic resonance data from a subject of which at least a part is located within an imaging volume, wherein the target volume is within the imaging volume, wherein the motion tracking magnetic resonance data has a higher temporal resolution than the image magnetic resonance data, wherein the method comprises receiving a treatment plan specifying the target volume within the imaging volume and a dose rate of radiation emitted by the radiotherapy apparatus, and in each of a plurality of fractions repeatedly:

controlling the radiotherapy apparatus to radiate the target volume in accordance with the treatment plan;

acquiring in an interleaved manner the higher temporal resolution motion tracking magnetic resonance data and the image magnetic resonance data by controlling the magnetic resonance scanner with an interleaved magnetic resonance pulse sequence;

calculating a dose distribution map descriptive of a radiation dose received by the subject from the radiotherapy apparatus;

reconstructing a diagnostic image using the image magnetic resonance data;

controlling a display to concurrently display the diagnostic image and the dose distribution map;

receiving treatment plan update data from a user interface; and updating the treatment plan in accordance with the treatment plan update data during the radiation of the target volume.

13. The method of claim 12, wherein the treatment plan update data includes a request to automatically update the treatment plan using the dose distribution map.

14. The method of claim 13, wherein the radiotherapy apparatus includes a multi-leaf collimator for collimating a radiation beam from the radiotherapy apparatus and wherein the treatment plan update data includes adjustments to the multi-leaf collimator to match the target volume.

15. The method of claim 14, wherein the step of acquiring the image magnetic resonance data is performed during a predetermined part of a cyclic cycle of the subject by controlling the magnetic resonance scanner.

16. The method of claim 15, wherein each repetition of the interleaved pulse sequence generates both the motion tracking magnetic resonance data and the image magnetic resonance data in an interleaved fashion.

17. The method of claim 16, wherein the image magnetic resonance data is acquired in a coronal view and positions of the target volume are continuously monitored in the coronal view.

* * * * *